(12) United States Patent
Kikkawa et al.

(10) Patent No.: US 8,563,235 B2
(45) Date of Patent: Oct. 22, 2013

(54) BIOMARKERS OF BILIARY TRACT CANCER

(75) Inventors: Shintaro Kikkawa, Chiba (JP);
Kazuyuki Sogawa, Chiba (JP); Osamu Yokosuka, Chiba (JP); Fumio Nomura, Chiba (JP)

(73) Assignee: National University Corporation Chiba University, Chiba (JP)

( * ) Notice: Subject to any disclaimer, the term of this patent is extended or adjusted under 35 U.S.C. 154(b) by 239 days.

(21) Appl. No.: 12/917,570

(22) Filed: Nov. 2, 2010

(65) Prior Publication Data
US 2011/0108722 A1    May 12, 2011

Related U.S. Application Data

(60) Provisional application No. 61/258,908, filed on Nov. 6, 2009.

(51) Int. Cl.
*C12Q 1/00* (2006.01)
*C12Q 1/56* (2006.01)
*C12N 9/74* (2006.01)

(52) U.S. Cl.
USPC .................................. 435/4; 435/13; 435/214

(58) Field of Classification Search
USPC ............................................................ 435/4
See application file for complete search history.

(56) References Cited

U.S. PATENT DOCUMENTS

2004/0219572 A1* 11/2004 Chen et al. .................. 435/6

OTHER PUBLICATIONS

Ebert, M, et al. "Identification of the Thrombin Light Chain A as the Single Best mass for Differentiation of Gastric Cancer from Individuals with Dyspepsia by bt Proteome Analysis" 2005 Journal of Proteome Research 4, 586-590.*
Matharoo-Ball, BW, et al. "Diagnostic biomarkers differentiating metastatic melanoma patients from healthy controls identified by an integrated MALDI-TOF mass spectrometry approach" 2007 Proteomics Clin. Appl. 1, 605-620.*
Nehls et al., "Serum and Bile Markers for Cholangiocarcinoma," Seminars in Liver Disease, vol. 24, No. 2, 2004, pp. 139-154 (16 pages).
Wadsworth et al., "Identification of Patients With Head and Neck Cancer Using Serum Protein Profiles," Arch Otolaryngol Head Neck Surg, vol. 130, Jan. 2004, pp. 98-104 (7 pages).
Rai et al., "Proteomic Approaches to Tumor Marker Discovery, Identification of Biomarkers for Ovarian Cancer," Arch Pathol Lab Med, vol. 126, Dec. 2002, pp. 1518-1526 (9 pages).
Rosty et al., "Identification of Hepatocarcinoma-Intestine-Pancreas/Pancreatitis-associated Protein I as a Biomarker for Pancreatic Ductal Adenocarcinoma by Protein Biochip Technology," Cancer Research, vol. 62, Mar. 15, 2002, pp. 1868-1875 (9 pages).
Koopmann et al, "Serum Diagnosis of Pancreatic Adenocarcinoma Using Surface-Enhanced Laser Desorption and Ionization Mass Spectrometry," Clinical Cancer Research, vol. 10, Feb. 1, 2004, pp. 860-868 (10 pages).
Suzuki et al., "Des-y-carboxy Prothrombin Is a Potential Autologous Growth Factor for Hepatocellular Carcinoma," The Journal Of Biological Chemistry, vol. 280, No. 8, Feb. 25, 2005, pp. 6409-6415 (7 pages).
Kuromatsu et al., "Usefulness of ED036 kit for measuring serum PIVKA-II levels in small hepatocellular carcinoma," Journal of Gastroenterology, vol. 32, 1997, pp. 507-512 (6 pages).
Zheng et al., "Experience of Congenital Choledochal Cyst in Adults: Treatment, Surgical Procedures and Clinical Outcome in the Second Affiliated Hospital of Harbin Medical University," J Korean Med Sci, vol. 19, 2004, pp. 842-847 (6 pages).
Petricoin et al., "Use of proteomic patterns in serum to identify ovarian cancer," The Lancet, vol. 359, Feb. 16, 2002, pp. 572-577 (6 pages).
Yu et al., "Prediction of Pancreatic Cancer by Serum Biomarkers Using Surface-Enhanced Laser Desorption/Ionization-Based Decision Tree Classification," Oncology, vol. 68, 2005, pp. 79-86 (9 pages).
Kozak et al., "Identification of biomarkers for ovarian cancer using strong anion-exchange ProteinChips: Potential use in diagnosis and prognosis," PNAS, vol. 100, No. 21, Oct. 14, 2003, pp. 12343-12348 (6 pages).

* cited by examiner

*Primary Examiner* — Manjunath Rao
*Assistant Examiner* — Gerard Lacourciere
(74) *Attorney, Agent, or Firm* — Kilyk & Bowersox, P.L.L.C.

(57) ABSTRACT

A method of detecting an abnormal amount of a biomarker associated with biliary tract cancer in a subject can comprise: a) quantitating an amount of a fragment of prothrombin having an m/z value of about 4204 m/z in a biological sample from the subject; and b) comparing the quantitated value obtained in (a) with a threshold value.

11 Claims, 6 Drawing Sheets

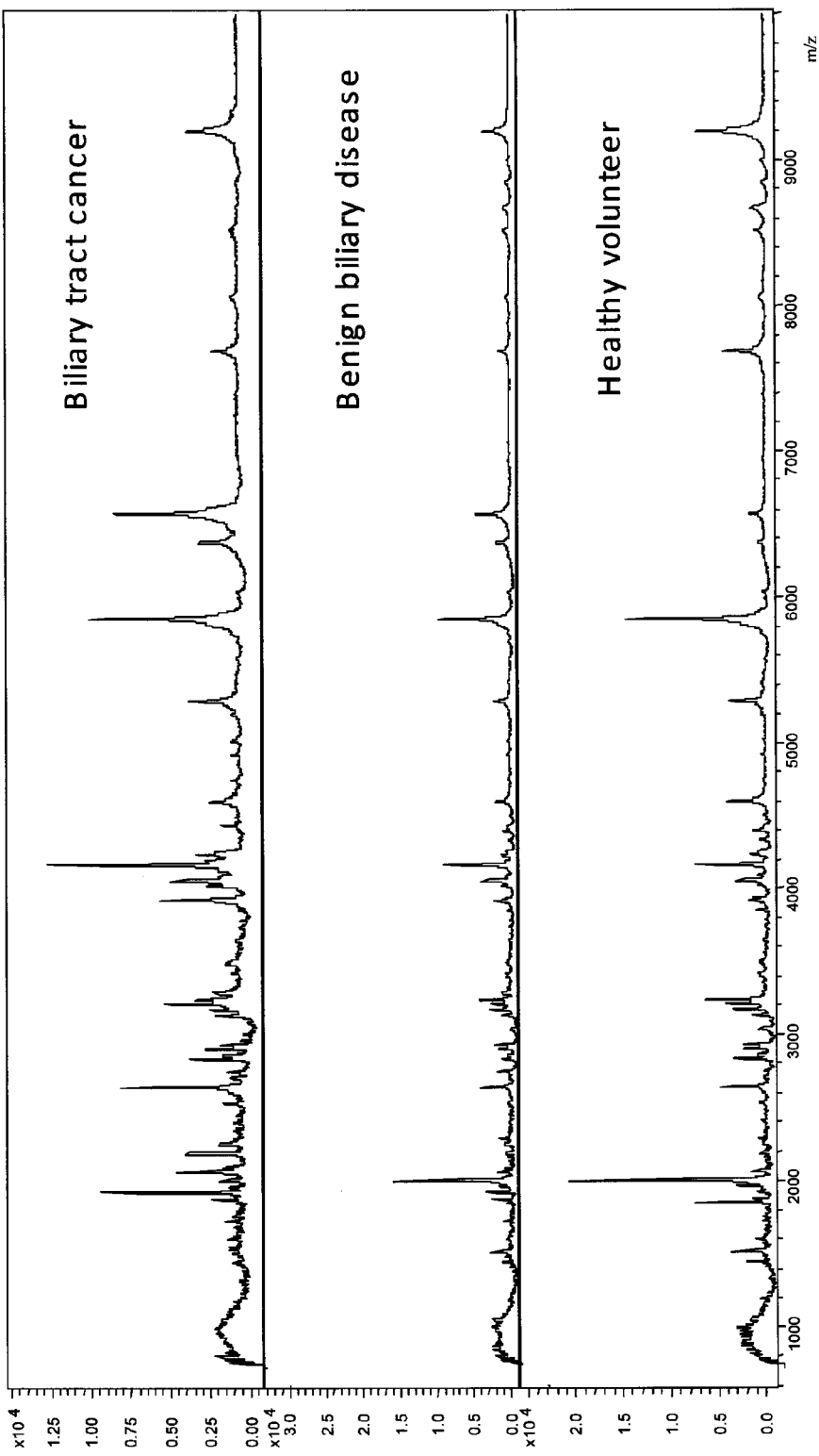
Fig 1. Representative mass spectra of serum samples obtained from patients with biliary tract cancer, Benign biliary disease, and Healthy volunteer

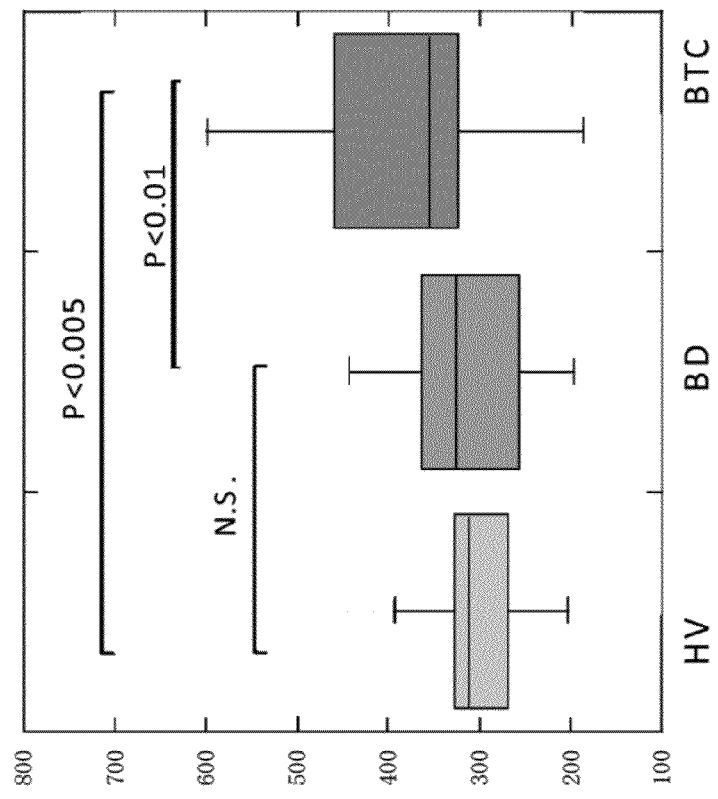
Fig 2. Normalized intensities of 4204 Da peptide were significantly increased in sera obtained from Biliary tract cancer (BTC) than in sera from healthy volunteers. In benign biliary disease (BB) sera, it wasnot significantly increased. (Mann-Whitney Utest).

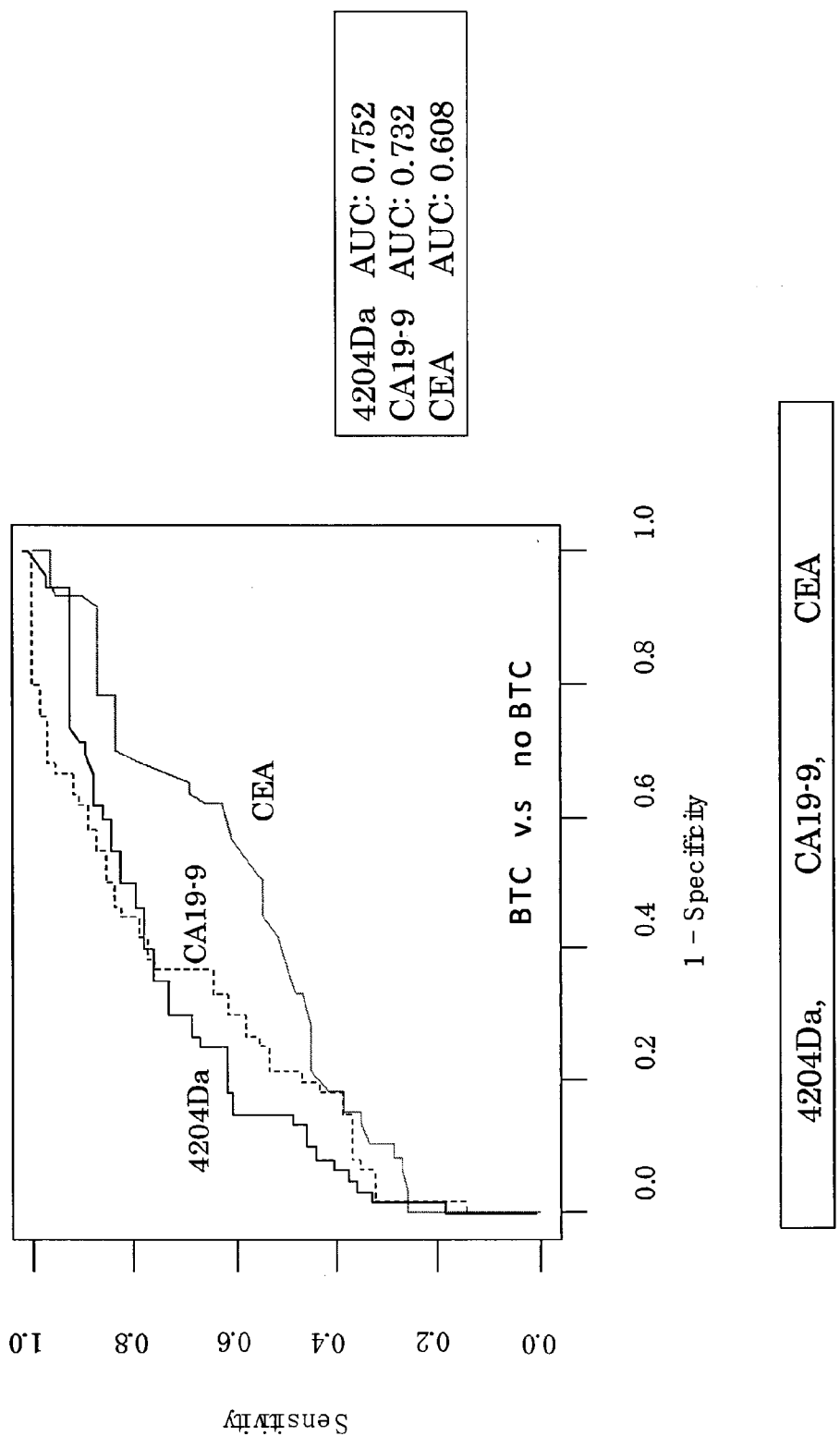
Fig 3a. ROC analysis of CEA, CA19-9, and 4204Da peptide

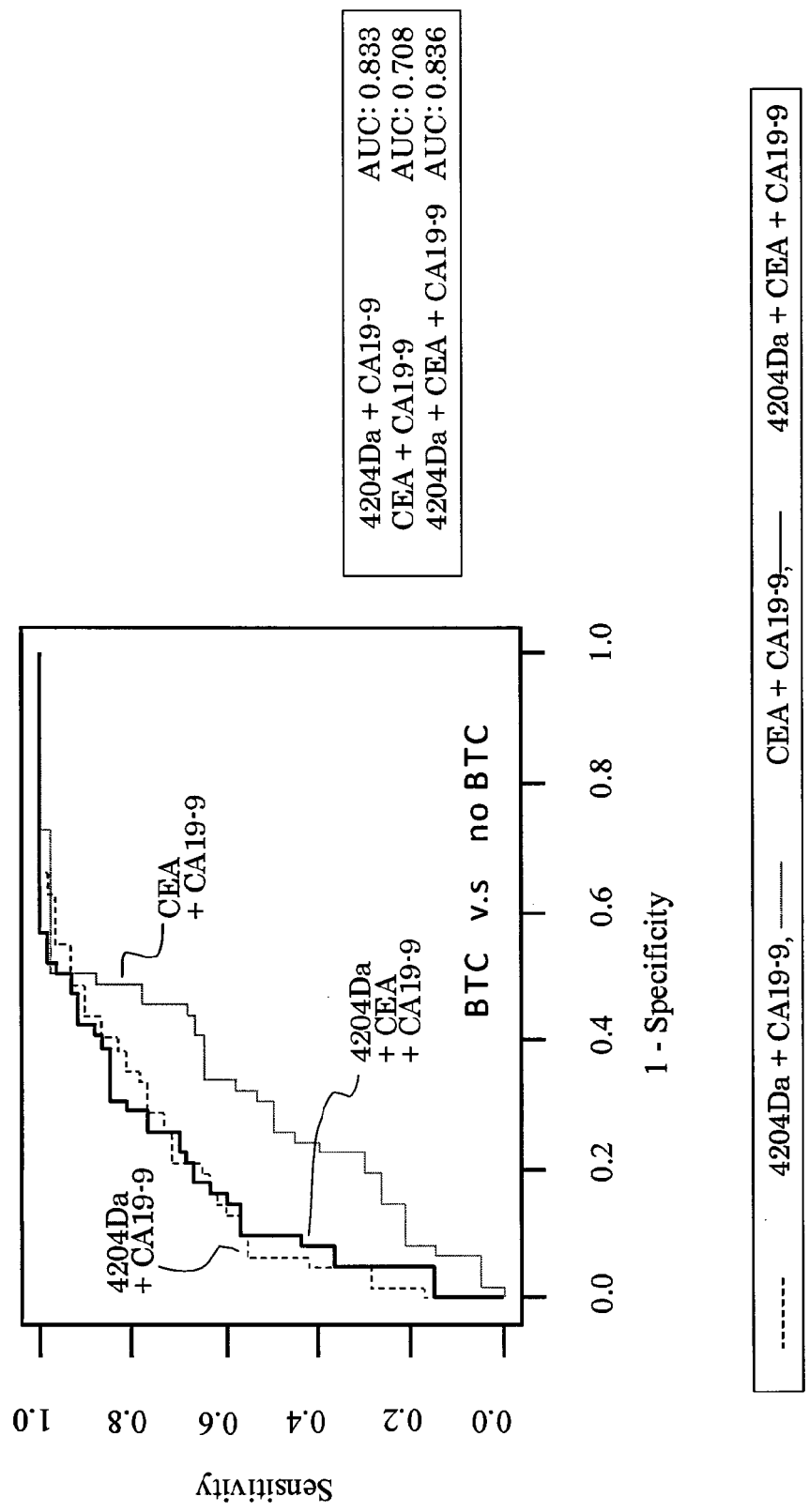

Fig 4. positive number of 4204Da peptide in CEA and CA19-9 negative BTC patients

| CEA (≧5 μg/mL) | CA19-9 (≧37U/mL) | 4204Da (≧322A.U) | N |
|---|---|---|---|
| − | − | − | 4 |
| − | − | + | 15 |
| − | + | − | 6 |
| + | − | − | 2 |
| + | + | − | 3 |
| + | − | + | 2 |
| − | + | + | 18 |
| + | + | + | 12 |

Fig 5. Purification of the 4204Da peptide
A) CM ceramic Hyper D F spin column
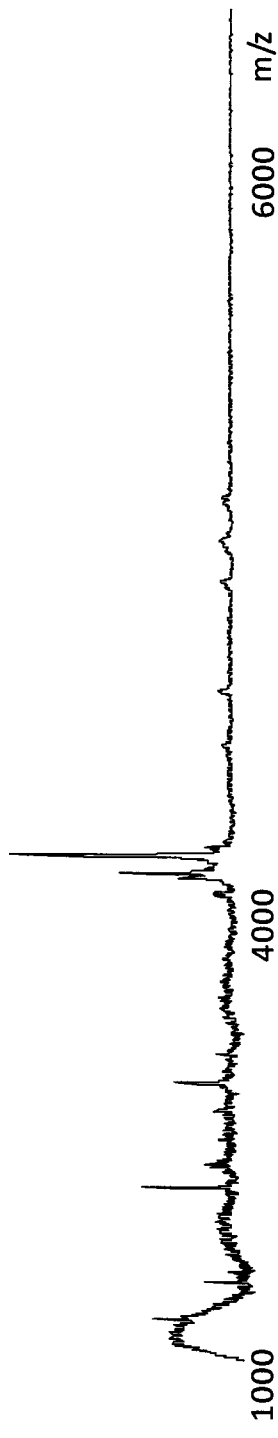
B) HPLC fraction
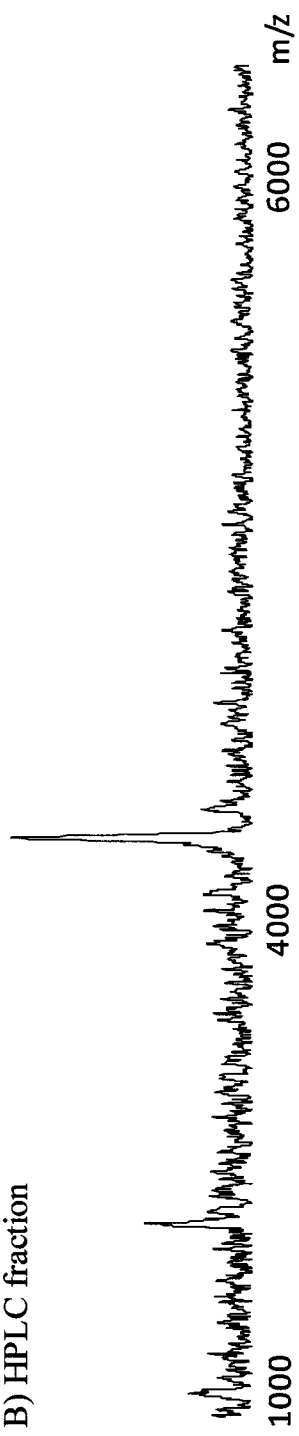

BIOMARKERS OF BILIARY TRACT CANCER

This application claims the benefit under 35 U.S.C. §119 (e) of prior U.S. Provisional Patent Application No. 61/258,908, filed Nov. 6, 2009, which is incorporated in its entirety by reference herein.

FIELD

The present invention relates to detecting novel biomarkers associated with biliary tract cancer and to detecting biomarkers associated with biliary tract cancer, for instance, using mass spectrometry.

BACKGROUND

Biliary tract cancer (BTC) is a neoplasm that accounts for 3% of all gastrointestinal cancers and 15% of all primary liver cancers. During the last two decades, the incidence of BTC is rising, mainly due to an increase in the intrahepatic form (Khan, S. A. et al., "Cholangiocarcinoma," *Lancet*, 366:1303-14 (2005); Patel, T. et al., "Cholangiocarcinoma," *Nat Clin Pract Gastroentel Hepatol*, 3:33-42 (2006)). North Thailand has the highest incidence (Shaib, Y. et al., "The epidemiology of holangiocarcinoma," *Semin Liver Dis*, 24:115-125 (2004)). Only chance to cure is complete surgical resection. For complete resection, diagnosis in early stage is important, but difficult. Even with margin free resection, 5-year survival figures only reach 20% to 40% (Jarmagin, W. R., et al., "Surgical management of cholangiocarcinoma," *Semin Liver Dis*, 24:18 (2004); Gores, G. J., "Cholangiocarcinoma: current concepts and insight," *Hepatology*, 37:961-969 (2003)). Unresectable disease usually shows 6-month to 1-year survival time (Jarmagin, W. R., et al., "Surgical management of cholangiocarcinoma," *Semin Liver Dis*, 24:18 (2004)). Almost one-third of the patients of BTC is too late for resection. Therefore, there is a need to establish a diagnostic process at the early stage of BTC.

Currently, diagnosis of BTC depends on imagings of the biliary tree such as computed tomography or ultrasonography or endscopic retrogradal cholangiograpy (ERC) in patients having clinical symptoms. Brush cytology by ERC can make a tissue diagnosis, but sensitivity is poor because of rich desemoplasitc nature of BTC (Gores, G. J., "Cholangocarcinoma: current concepts and insight," *Hepatology*, 37:961-969 (2003); Abu-Hamda, E. M., et al., "Endoscopic management of cholagiocarcinoma," *Semin Liver Dis*, 4:165-175 (2004)). Consequently clinicians often elucidate other diagnostic clues of malignancy, and tumor markers provide more information.

Serum tumor markers, carcinoembryonic antigen (CEA) and carbon hydrate antigen 19.9 (CA19-9) are used worldwide for diagnosis of BTC but they have poor sensitivity and specificity. Many reports represent the specificity of these markers are respectively 50% and 70% (Nehls, O. et al., "Serum and Bile markers for cholangiocarcinoma," *Semin Liver Dis*, 24:139-154 (2004)). Therefore, there is a need for new markers of BTC. Before now, a proteomic technique has been used with a number of other malignancy to discover potential markers such as ovarian (Rai, A. J. et al., "Proteomic approaches to tumor marker discovery," *Arch Pathol Lab Med*, 126:1518-1526 (2002); Kozak, K. R., et al., "Identification of biomarkers for ovarian cancer using strong anionex-change Protein chip," 100:12343-12348 (2003); Petricoin, E. F., et al., "Use of proteomic patterns in serum to identify ovarian cancer," *Lancet*, 359:572-577, (2002)), pancreatic (Rosty, C. et al., "Identification of hepatocarcinoma-intestine-pancreas/pancreatitis-associated protein I as a biomarker for pancreatic ductal adenocarcinoma by protein biochip technology," *Cancer Res*, 62:1868-1875 (2002); Koopmann, J, et al., "Serum diagnosis of pancreatic adenocarcinoma using surface-enhanced laser desorption and ionization mass spectrometry," *Clin Cancer Res*, 10:860-868 (2004); Yu, Y., et al., "Prediction of pancreatic cancer by serum biomarkers using surface-enhanced laser desorption/ionization-based decision tree classification," *Oncology*, 68:79-86 (2005), head and neck (Yu, Y. et al., "Prediction of pancreatic cancer by serum biomarkers using surface-enhanced laser desorption/ionization-based decision tree classification," *Oncology*, 68:79-86 (2005); Wadsworth, J. T. et al., "Identification of patients with head and neck cancer using serum protein profiles," *Arch Otolarygol Head Neck Surg*, 130:98-104 (2004)), using SurfaceEnhancedlaser Desorption and Ionization Mass Spectrometry (SELDI-TOF-MS).

Matrix-assisted laser desorption/ionization time-of-flight (MALDI-TOF) represents a key tool for rapidly analyzing clinical blood samples. The advantages of this method are its high-throughput capability and small sample size necessary for the analysis. Therefore, the inventors sought to identify a new biomarker of BTC with this technique and analyzed the serum profiling of the low molecular weight peptides with MALDI-TOF mass spectrometry in patients with BTC.

SUMMARY

A method of detecting an abnormal amount of a biomarker associated with biliary tract cancer in a subject is provided. The method of detecting an abnormal amount of a biomarker associated with biliary tract cancer in a subject can comprise: a) quantitating an amount of a fragment of prothrombin having an m/z value of about 4204 m/z in a biological sample from the subject using mass spectrometry; and b) comparing the quantitated value obtained in (a) with a threshold value. An abnormal amount of the biomarker can be present in the biological sample when the quantitated value exceeds the threshold value. The biomarker can be a fragment of prothrombin having the amino acid sequence of SEQ ID NO: 2. An abnormal amount of the fragment of prothrombin can indicate that the subject has biliary tract cancer. The mass spectrometry technique which can be used to detect the biomarker can be matrix-associated laser desorption ionization time-of-flight mass spectrometry MALDI-TOF MS. The biological sample can be blood serum or other suitable sample. The threshold value can be at least 322 AU.

A method for identifying a biomarker to detect biliary tract cancer can comprise: a) generating mass spectra for biological samples taken from patients with biliary tract cancer, patients with benign biliary disease, and healthy patients; and b) comparing the spectra generated in (a); and c) identifying a mass spectrometric peak that is significantly higher in mass spectra for biliary tract cancer patients than in mass spectra for patients with benign biliary disease, and healthy patients.

A method of detecting biliary tract cancer in a subject can comprise: a) quantitating an amount of a fragment of prothrombin in a sample from the subject using mass spectrometry, wherein the fragment of prothrombin has an m/z value of about 4204 m/z; and b) comparing the quantitated value obtained in (a) with a threshold value; wherein biliary tract cancer is detected when the quantitated value exceeds the threshold value. The mass spectrometry can be matrix-associated laser desorption ionization time-of-flight mass spectrometry (MALDI-TOF MS). The method can comprise quantitating at least one additional biomarker in the sample from the subject. The at least one additional biomarker can be carbohydrate antigen 19-9 (CA 19-9). The at least one additional biomarker can be carcinoembryonic antigen (CEA).

It is to be understood that both the foregoing general description and the following detailed description are exemplary and explanatory only and are intended to provide a further explanation of the present invention, as claimed.

All the patents and publications mentioned above and throughout are incorporated in their entirety by reference herein, including Sobin L. H. et al., *TNM Classification of Malignant Tumors*, 5th edition (1997), Union Internationale Contre le Cancer and American Joint Committee on Cancer, 80:1803-1804 (1977).

The accompanying drawings, which are incorporated in and constitute a part of this application, illustrate some of the features of the present invention and together with the description, serve to explain the principles of the present invention.

The present teachings will be described with reference to the accompanying drawings. The drawings are intended to illustrate, not limit, the present teachings.

BRIEF DESCRIPTION OF THE DRAWINGS

FIG. 1 shows a segment of the protein mass profile between m/z 0 and 10000 highlighting the differentially expressed peaks between serum from healthy volunteers, benign biliary disease, and BTC patients. The m/z 4,204 peak is upregulated in cancer patients when compared with benign patients and healthy volunteers.

FIG. 2 shows normalized intensities of 4204 Da peptide were significantly increased in sera obtained biliary tract cancer (BTC) than in sera from healthy volunteers. In benign biliary disease (BB) sera, it was not significantly increased. (Mann-Whitney U test).

FIG. 3a shows ROC analyses for the performance of m/z 4204, CA19-9, and CEA. AUC values=0.752 for m/z 4204 peak and 0.732 for CA19-9 and 0.608 for CEA.

FIG. 3b shows ROC analyses for the performance of m/z 4204, CA19-9, and CEA. AUC values=0.833 for m/z 4204 peak+CA19-9, 0.708 for CA19-9+CEA, and 0.836 for m/z 4204 peak+CEA+CA19-9.

FIG. 4 shows the positive number 4204 peptide in CEA and CA19-9 negative BTC patients.

FIG. 5 shows purification of the 4204 Da peptide. (A) Crude serum was subjected to ion-exchange fractionation by CM ceramic Hyper D F spin column. (B) The partially purified fraction was subjected to the second HPLC, resulting in successful purification of the 4204 Da peptide.

DETAILED DESCRIPTION

A method of detecting an abnormal amount of a biomarker associated with biliary tract cancer in a subject is provided. The method can comprise: a) quantitating an amount of a fragment of prothrombin having an m/z value of about 4204 m/z in a biological sample from the subject using mass spectrometry; and b) comparing the quantitated value obtained in (a) with a threshold value. An abnormal amount of the biomarker can be present in the biological sample when the quantitated value exceeds the threshold value.

The biomarker can be a fragment of prothrombin. The fragment of prothrombin can have an m/z value ranging from about 4200 m/z to about 4210 m/z. The fragment of prothrombin can have an m/z value of about 4204 m/z. The fragment of prothrombin can have an amino acid sequence comprising the amino acid sequence of SEQ ID NO: 2. The fragment of prothrombin can include only the amino acid sequence of SEQ ID NO: 2. The fragment of prothrombin can include an amino acid sequence having at least 80% homology with the amino acid sequence of SEQ ID NO: 2. The fragment of prothrombin can include an amino acid sequence having at least 85% homology with the amino acid sequence of SEQ ID NO: 2. The fragment of prothrombin can include an amino acid sequence having at least 90% homology with the amino acid sequence of SEQ ID NO: 2. The fragment of prothrombin can include an amino acid sequence having at least 95% to 99% homology with the amino acid sequence of SEQ ID NO: 2.

An abnormal amount of the biomarker can be present in the biological sample when the quantitated value exceeds a threshold value. The biological sample can be blood, serum, urine, prostatic fluid, seminal fluid, semen, tissue extract sample, or biopsy. The threshold value can be at least 322 AU (arbitrary units). An abnormal amount of the fragment of prothrombin can indicate that the subject has biliary tract cancer.

The biomarker in the biological sample can be quantitated using mass spectrometry. The mass spectrometry, which can be used to quantify the biomarker, can be matrix-assisted laser desorption ionization/time of flight (MALDI-TOF), surface enhanced laser desorption ionization time of flight (SELDI-TOF), liquid chromatography, tandem mass spectrometry (MS-MS), electrospray ionization (ESI-MS), or desorption electrospray ionization (DESI). The mass spectrometry can be matrix-associated laser desorption ionization time-of-flight mass spectrometry MALDI-TOF MS.

A biomarker to detect biliary tract cancer can be identified by: a) generating mass spectra for biological samples taken from patients with biliary tract cancer, patients with benign biliary disease, and healthy patients; and b) comparing the mass spectra of the patients with biliary tract cancer, patients with benign biliary disease, and healthy patients; and c) identifying a mass spectrometric peak that is significantly higher in mass spectra for biliary tract cancer patients than in mass spectra for patients with benign biliary disease, and healthy patients. A mass spectrometric peak that is significantly higher or, in other words, a peptide peak that is significantly upregulated can be determined by one of ordinary skill in the art. An average increase of at least 50 A.U. for patients with biliary tract cancer can be deemed significant, for example.

Biliary tract cancer in a subject can be detected by: a) quantitating an amount of a fragment of prothrombin in a sample from the subject using mass spectrometry, wherein the fragment of prothrombin has an m/z value of about 4204 m/z; and b) comparing the quantitated value with a threshold value. Biliary tract cancer can be detected when the quantitated value exceeds the threshold value. The mass spectrometry can be matrix-associated laser desorption ionization time-of-flight mass spectrometry (MALDI-TOF MS). The method can comprise quantitating at least one additional biomarker in the sample from the subject. The at least one additional biomarker can be carbohydrate antigen 19-9 (CA 19-9). The at least one additional biomarker can be carcinoembryonic antigen (CEA).

The present invention includes the following aspects/embodiments/features in any order and/or in any combination:
1. The present invention relates to a method of detecting an abnormal amount of a biomarker associated with biliary tract cancer in a subject comprising: a) quantitating an amount of a fragment of prothrombin having an m/z value of about 4204 m/z in a biological sample from the subject using mass spectrometry; and b) comparing the quantitated value obtained in (a) with a threshold value; wherein an abnormal amount of the biomarker is present in the biological sample when the quantitated value exceeds the threshold value.

2. The method of any preceding or following embodiment/feature/aspect, wherein the biomarker is a fragment of prothrombin having the amino acid sequence of SEQ ID NO: 2.

3. The method of any preceding or following embodiment/feature/aspect, wherein an abnormal amount of the fragment of prothrombin indicates that the subject has biliary tract cancer.

4. The method of any preceding or following embodiment/feature/aspect, wherein the mass spectrometry is matrix-associated laser desorption ionization time-of-flight mass spectrometry MALDI-TOF MS.

5. The method of any preceding or following embodiment/feature/aspect, wherein the biological sample is blood serum.

6. The method of any preceding or following embodiment/feature/aspect, wherein the threshold value is at least 322 AU.

7. A method for identifying a biomarker to detect biliary tract cancer comprising: a) generating mass spectra for biological samples taken from patients with biliary tract cancer, patients with benign biliary disease, and healthy patients; and b) comparing the spectra generated in (a); c) identifying a mass spectrometric peak that is significantly higher in mass spectra for biliary tract cancer patients than in mass spectra for patients with benign biliary disease, and healthy patients.

8. A method of detecting biliary tract cancer in a subject comprising: a) quantitating an amount of a fragment of prothrombin in a sample from the subject using mass spectrometry, wherein the fragment of prothrombin has an m/z value of about 4204 m/z; and b) comparing the quantitated value obtained in (a) with a threshold value; wherein biliary tract cancer is detected when the quantitated value exceeds the threshold value.

9. The method of any preceding or following embodiment/feature/aspect, wherein the mass spectrometry is matrix-associated laser desorption ionization time-of-flight mass spectrometry (MALDI-TOF MS).

10. The method of any preceding or following embodiment/feature/aspect, further comprising quantitating at least one additional biomarker in the sample from the subject.

11. The method of any preceding or following embodiment/feature/aspect, wherein the at least one additional biomarker is carbohydrate antigen 19-9 (CA 19-9).

12. The method of any preceding or following embodiment/feature/aspect, wherein the at least one additional biomarker is carcinoembryonic antigen (CEA).

The present invention can include any combination of these various features or embodiments above and/or below as set forth in sentences and/or paragraphs. Any combination of disclosed features herein is considered part of the present invention and no limitation is intended with respect to combinable features.

The present invention will be further clarified by the following examples, which are intended to be exemplary of the present invention.

EXAMPLES

The present teachings can be even more fully understood with reference to the examples and resulting data that follow.

Methods
Patients and Blood Sample Preparation.
Sera were collected from 62 patients with biliary tract cancer (36 men, median age 64.7 years, range 27-81 years). Sera from 30 healthy volunteers (18 men, median age 65.5 years, range 61-69 years) served as normal controls. As disease controls, sera from 30 patients with benign biliary disease (18 men, median age 64.4 years, range 27-90 years) were collected. All the patients with biliary tract cancer were diagnosed by radiological imagings or cytology. All of patients with benign biliary disease were followed up more than 12 month and it was confirmed that they had no malignancy. After taking blood samples, they were allowed to clot at the room temperature for about 2 hours, and centrifuged at 1200 g for 15 minutes. Sera were stored in aliquots at −80° C. Table 1 shows the patient's clinicopathological details. Intarhepatic cholangicocarcinomas (n=17), Klaskin tumors (n=7), extraheptaic cholangiocarcinomas (n=16), Papilla Vater tumors (n=6), gallbladder tumor (n=16). The 62 BTC samples were classified into pathological stages according to the Union Internationale Contre le Cancer tumor node metastasis classification of staging (P). They comprised 16 early-stage (stage I, n=6; stage II, n=10), 46 late-stage (stage III, n=16; stage IV, n=30).

TABLE 1

Clinical characteristics of patients with biliary tract cancer benign biliary disease, and healthy volunteers

|  | Biliary tract cancers | Benign biliary diseases | Healthy volunteers |
| --- | --- | --- | --- |
| No. patients | 62 | 30 | 30 |
| Male/female | 36/26 | 18/12 | 18/12 |
| Mean age | 64.7 ± 37.4 | 64.4 ± 39.0 | 65.5 ± 4.5 |
| Location |  |  |  |
| Extrahepatic | 16 |  |  |
| Intrahepatic | 17 |  |  |
| Klatskin | 7 |  |  |
| Papilla vater | 6 |  |  |
| Gall bladder | 16 |  |  |
| UICC stage |  |  |  |
| Stage I | 6 |  |  |
| Stage II | 10 |  |  |
| Stage III | 16 |  |  |
| Stage IV | 30 |  |  |
| Benign biliary disease |  |  |  |
| Cholelithiasis |  | 24 |  |
| Benign fibrous stricture |  | 4 |  |
| Primary sclerosing cholangitis |  | 2 |  |
| CEA (ng/mL) | 37.6 ± 1577.3 | 2.53 ± 3.57 | 3.1 ± 3.5 |
| CA19-9 (U/mL) | 5033.6 ± 190367.2 | 70.42 ± 603.9 | 15.3 ± 18.6 |

A benign biliary group 30 patients undergoing endoscopic retrogradae cholangiopancreatography for a benign biliay condition (cholelithiasis, n=24; benign fibrous stricture, n=4; primary sclerosing cholangitis; n=2). Healthy volunteer group comprised serum from 30 healthy volunteers who had had no general practitioner visit or hospital admission for six month. All samples underwent biochemistry test to measure the amount of total protein and albumin, as well as liver function test, including alkaline phosphatase, aspirate aminotransferase, alanine aminotransferase, γ-glutamyl-transpeptidase, total bilirubin, direct bilirubin, C-reactive protein and the tumor markers CA19.9 and CEA.

Serum Pretreatment with WCX Magnetic Beads by ClinProtRobot.
Serum samples (5 μl) were prefractionated using Magnetic Beads based Weak Cation Exchange Chromatography resins (MB-WCX) (Bruker Daltonics, Germany) by ClinProt™ Robot automatic machine. A 5 μl serum sample was mixed with 10 μl binding solution, then 5 μl MB-WCX was added and the solution was mixed. Next, the tube was placed in a magnetic bead separator to allow separation of the unbound solution and the supernatant was removed. The beads were then washed three times with 100 μl wash buffer and afterwards proteins and peptides were eluted from the magnetic beads with 10 μl of elution solution and 10 μl stabilization solution. The eluate was diluted 1:10 in CHCA matrix solution (Bruker Daltonics, Germany). Then 1 μl of the mixture was spotted onto an AnchorChip™ target (Bruker Daltonics, Germany) and was left for several minutes at room temperature until dry up. All procedures were performed according to the protocols described elsewhere (Umemura, H. et al., "Effects of the time intervals between venipuncuture and serum preparation for serum peptidome analysis by matrix-assisted laser desorption/ionization time-of-flight mass spectrometry," *Clinica Chimica Acta*, 406:179-180 (2009); Sogawa, K. et al. "A search for novel markers of alcohol abuse using magnetic beads and MALDI-TOF/TOF mass spectorometry," *Proteomics Clin. Appl.*, 3:821-828 (2009)).

Chemicals and Calibrators.

2-cyano-4-hydroxycinnamic acid (CHCA) matrix solution (Bruker Daltonics, Bremen, Germany) was diluted as 0.3 g/l in ethanol:acetone (2:1) solution. Acetone and ethanol were HPLC-grade and purchased from Wako Pure Chemical Industries (Osaka, Japan). Calibrator was Peptide Calibration Standard II (Bruker Daltonics, Bremen, Germany).

Mass Spectrometry.

The AnchorChip™ target plate was placed in an AutoFlex® II TOF/TOF mass spectrometer (Bruker Daltonics, Germany) controlled by Flexcontrol™ 2.4 software (Bruker Daltonics, Germany). The instrument is equipped with a 337 nm nitrogen laser, delayed-extraction electronics, and a 25 Hz digitizer. All acquisitions were generated by an automated acquisition method included in the instrument software and based on averaging 1000 randomized shots. Spectra were acquired in positive linear mode, in the mass range of 600-10000 Da. Peak clusters were completed using second pass peak section (signal to noise ratio>5). The relative peak intensities, normalized to a total ion current of m/z between 600 and 10000 were expressed as arbitrary unit. All the spectra ranged from 1000 to 4000 m/z obtained from MALDI-TOF MS were analyzed with Bruker Daltonics flexAnalysis 2.1 software and ClinProtools 2.1 software.

Protein Identification.

A serum sample was prefractionated using CM ceramic Hyper D F spin column (Bio-RAD). Briefly, the column was washed by Binding buffer (400 μl) three times. A 40 μl serum sample was mixed with 160 μl binding buffer, then was added into the column and mixed. Next, the column was incubated at 4° C. for 1 hour and centrifuged 80 G for 1 minute, then the supernatant was removed. The column was then washed three times with 400 μl wash buffer and afterwards proteins and peptides were eluted from the columns with 40 μl of elution solution. The eluate was mixed with 1:10 in Aceton and incubated at −20° C. for 2 hours. Then, the mixture was centrifuged at 20000 g for 10 minutes and the supernatant was removed. The sediment was resuspended with 0.1% TFA and applied to reverse phase columns for further separation from other proteins and fractionation. The fraction including objective peak were confirmed by MALDI-TOF MS, analysed by N-terminal amino-acid sequence.

Statistical Analysis.

Univariate analysis of individual peaks was performed using the nonparametric Maim-Whitney U test: P value<0.05 discriminatory power for putative marker was further described via receiver operating characteristic (ROC) area under the curve (AUC) analysis using statFlex 5.0 (Artech Inc., Osaka, Japan).

Results

MALDI-TOF-MS Analysis of Peptides in Sera of BTC.

At first, the low molecular peptide spectra obtained from biliary tract cancer was compared with those of normal controls and benign biliary disease (training set). Peak intensities of 23 peptides were significantly different in the BTC and normal control groups; of the 23 peptides, fifteen were upregulated and eight were downregulated in the BTC group (Table 2a). Then, the peptide profiling between BTC group and benign biliary disease group and normal control group (test set) was compared by using MALDI-TOF mass spectrometry. Peak patterns of BTC group and benign biliary disease group and normal control group were significantly different (FIG. 1). Among the 23 peptide peaks, which were different in BTC and normal benign biliary disease, and different in BTC and normal control group, the intensity of only one peptide peak with a m/z value of 4204 Da was significantly upregulated in the BTC group (Table 2b). FIG. 2 shows that serum level of the 4204 Da peptide significantly increased in BTCs sera (mean 388.84 AU: p<0.001), compared with normal control sera (mean 316.06 AU). In benign biliary disease, it was not increased (mean 317.36 arbitrary unit: p<0.01).

TABLE 2a significant different peak in a training set

| Increased in cholangiocarcinma group | | Decreased in cholangiocrcinoma group | |
|---|---|---|---|
| m/Z | P value | m/Z | P value |
| 1207 (Cu) | <0.0001 | 1944 (W) | <0.0001 |
| 1466 (Cu) | <0.0001 | 2659 (W, Cu) | <0.001 |
| 3261 (Cu) | <0.001 | 2931 (Cu) | <0.0001 |
| 3950 (W) | <0.001 | 3239 (W, Cu) | <0.0001 |
| 4204 (W) | <0.001 | 3272 (W) | <0.001 |
| 4635 (W) | <0.001 | 3878 (Cu) | <0.01 |
| 4654 (W) | <0.001 | 4051 (W, Cu) | <0.001 |
| 5791 (W, Cu) | <0.0001 | 4086 (Cu) | <0.0001 |
| 5890 (W, Cu) | <0.0001 | 4276 (W) | <0.0001 |
| 5929 (W) | <0.001 | 6414 (W) | <0.001 |
| 9246 (W) | <0.001 | | |
| 9285 (W) | <0.005 | | |

TABLE 2b significantl different peaks in training and test set

| Increased in cholangiocarcinma group | | Decreased in cholangiocrcinoma group | |
|---|---|---|---|
| m/Z | P value | m/Z | P value |
| 4204 (W) | <0.01 | 3272 (W) | <0.05 |

(Mann-Whitney U test)

Analysis of the diagnostic accuracy of CA19-9, CEA, 4204 Da was made by receiver operating characteristics (FIG. 3a). The area under the curve were 0.732 for CA19-9, 0.608 for CEA, 0.752 for 4204 Da in patients with biliary tract cancer versus healthy volunteers and benign biliary disease.

The discriminary power of this approach was further improved by including the tumor markers CA19-9 and CEA. ROC values of these combinations are shown in FIG. 3b. ROC values were 0.833 for m/z4204+CA19-9, 0.836 for m/z4204+CEA+CA19-9, 0.708 for CEA+CA19-9 in patients with biliary tract cancer versus healthy volunteers and benign biliary disease.

The positive rate of 4204 Da peptide of CEA, CA19-9 negative BTC patients (FIG. 4) was assessed. Nineteen patients of 62 BTC patients showed CEA, CA19-9 double negative. Of these patients, 15 patients (79%) showed 4204 Da peptide positive if the cut-off value was set at 322 A.U.

Identification of 4204 Da as a Fragment of Prothrombin by CM Ceramic Hyper D F Spin Column, Acetic Precipitation, HPLC Fractionation and N-Terminal Amino Acid Sequence Analysis.

The peak of the 4204 Da peptide relatively had a high mass spectrometric peak height, clear separation from other peaks, and significantly high expression in biliary tract cancer patients. To purify and identify the 4204 Da peptide, serum sample was fractionated on CM ceramic Hyper D F spin column. After the elute was precipitated by aceton, the sediment was resuspended with 0.1% TFA and applied to revease phase columns for further separation from other proteins, and the fractionation was carried out with stepwise gradient, using high performance liquid chromatography (HPLC). Using these procedures, the target 4204 Da peptide was successfully purified (FIG. 5).

N-terminal amino-acid sequence analysis of purified peptide revealed that it was a fragment of prothrombin. This analysis was carried out with identifying the 10 amino acids on the N terminus (Table 3).

patients with benign biliary disease and healthy volunteers was more accurate than traditional biomarkers in identifying BTC.

The need for better marker for the diagnosis of biliary tract cancer is an important target for clinical researchers. Proteomics represents a potentially powerful tool for the serologic recognition of protein profiles associated with cancer. The low molecular weight portion of the proteome, previously hidden by the limited resolution of 2-dimensional gel electrophoresis, appears to carry an abundance of tumor specific information with the potential to improve both diagnosis and the understanding of tumor pathogenesis. MALDI-TOF MS, a proteomic approach searching the low molecular weight portion of the proteome, may by itself not only be used as a discovery tool, but also be diagnostic tool itself. In this study, using a MALDI-TOF MS analysis, novel serum biomarkers was found among low molecular weight peptides in biliary tract cancer, and this peptide was identified as a fragment of prothrombin with a molecular weight of 4204 Da.

Serum CA19-9 and CEA level have been used as markers for biliary tract cancer. Their use in BTC was recently evaluated by Nehls et al. (Nehls, O. et al., "Serum and Bile markers for cholangiocarcinoma," *Semin Liver Dis*, 24:139-154 (2004)). They reported an average sensitivity of 71% and 51% and an average specificity of 78% and 88%. It is the most

TABLE 3

N-terminal amino acid sequence of purified fraction
Prothrombin fragment

SEQ ID NO: 1

MAHVRGLQLP GCLALAALCS LVHSQHVFLA PQQARSLLQR VRRANTFLEE VRKGNLEREC

VEETCSYEEA FEALESSTAT DVFWAKYTAC ETARTPRDKL AACLEGNCAE GLGTNYRGHV

NITRSGIECQ LWRSRYPHKP EINSTTHPGA DLQENFCRNP DSSTTGPWCY TTDPTVRRQE

CSIPVCGQDQ VTVAMTPRSE GSSVNLSPPL EQCVPDRGQQ YQGRLAVTTH GLPCLAWASA

QAKALSKHQD FNSAVQLVEN FCRNPDGDEE GVWCYVAGKP GDFGYCDLNY CEEAVEEETG

DGLDEDSDRA IEGRTATSEY QTFFNPRTFG SGEADCGLRP LFEKKSLEDK TERELLESYI

DGRIVEGSDA EIGMSPWQVM LFRKSPQELL CGASLISDRW VLTAAHCLLY PPWDKNFTEN

DLLVRIGKHS RTRYERNIEK ISMLEKIYIH PRYNWRENLD RDIALMKLKK PVAFSDYIHP

VCLPDRETAA SLLQAGYKGR VTGWGNLKET WTANVGKGQP SVLQVVNLPI VERPVCKDST

RIRITDNMFC AGYKPDEGRR GDACEGDSGG PFVMKSPFNN RWYQMGIVSW GEGCDRDGKY

GFYTHVFRLK KWIQKVIDQF GE

Notes:
Bold letters were the part identified by N-terminal sequence
Total molecular weight of under lined (SEQ ID NO: 2) was 4204 Da Discussion Matrix-associated laser desorption ionization time-of-flight mass spectrometry (MALDI-TOF-MS) is a proteomic technique that can identify a novel biomarker in serum and any biological fluid. This technique was used to identify new biomarkers of biliary tract cancer (BTC) because it is difficult to diagnose and has poor prognosis. Sera from 62 patient of BTC, and 30 benign biliary disease and 30 healthy volunteers were analyzed by ClinProt™ system (Bruker Daltonics Inc). The most efficient protein peak to discriminate of patient with CC is mass-to-charge 4204 (p<0.05). m/z 4204 had superior discriminary ability to carbohydrate antigen 19-9 (CA19-9) and carcinoembryonic antigen (CEA). (Area under the curve [AUC]=0.752, 0.732, 0.608). Sequential amino acid analysis identified this peptide to be a prothrombin fragment. MALDI-TOF-MS accurately distinguished patients with BTC from interesting discovery in this study that MALDI-TOF MS peak (m/z 4204) was as effective at discriminating cancer from benign serum such as the tumor markers CEA or CA19-9, and the combination of these markers significantly improved classification.

It is thought that biliary tract cancer arise on a background of continuous inflammation in biliary tree. The presence of gallstones, choledochal cyst, sclerosing cholangitis brings out this inflammation (Zheng, L. X. et al., "Experience of congenital choledochal cyst in adults; treatment, surgical procedures and clinical outcome in the Second Affiliated Hospital of Harbin Medical University," *J Korean Med Sci*, 19:842-847 (2004); Cullen, S. N. et al., "Review article: current management of primary sclerosing cholangitis," *Aliment Pharmacol Ther*, 21:933-948 (2005)). Alterations in the serum protein profile would seem likely as a result of both the malignant process itself and secondary to the inflammatory response including release of cytokines and acute phase proteins from the liver. It was therefore important to have a control group of patients who did not have cancer but who had a variety of biliary inflammatory process with matched liver dysfunction.

Recently, many studies using proteomic approach such as MALDI-TOF MS and SELDI-TOF MS showed protein-expression of neoplasms, but these have not been developed to clinical application. Some studies have reported that biomarker panels with combination of some protein peaks have been useful. Biomarker panels were complicated and difficult to use at clinical situation. Therefore, a simple biomarker was elucidated and identified as a prothrombin fragment as m/z 4204 peptide.

Prothrombin, the precursor of α-thrombin, is synthesized in the hepatocytes and is gamma-carboxylated at its amino terminal end by a vitamin K-dependent carboxylase (Mann, K. G. et al., "Surface-dependent reactions of the vitamin K-dependent enzyme complexes," Blood, 76:1-16 (1990)). This carboxylation reaction is defective in hepatocelluer carcinoma (HCC) tissues and they secrete des-gammmacarboxy prothrombin (Kuromatsu, R. et al, "Usefulness of ED036 kit for measuring serum PIVKA-II levels in small hepatocellular carcinoma," J Gastroenterol, 32:507-512 (1997)). DCP has been recently shown to act as a stimulant for hepatoma cell growth (Suzuki, M. et al., "Des-γ-carboxy prothrombin is a potential autlogus growth factor for hepatocellular carcinoma," J Biol Chem, 280:6409-6415 (2005)).

Although a fragment of prothrombin was identified as a new biomarker of CC, the mechanism of resolution of prothrombin was unknown. It is possible that CC tissues secret a fragment of prothrombin such as DCP. Because 4204 Da peptide isn't affected by the time intervals between venipuncture and serum preparation, and freezing methods (Q), clinical application is hoped.

In this study, a new strategy based on the proteomic approach was used. Serum proteins were identified that were highly expressed in patients with cholangiocarcinoma. The importance to analyze the low molecular weight peptides which had not yet been detected by conventional techniques is shown herein. Mass spectrometry could introduce to testing small peptides, and provides new insight into the pathophysiology in a variety of hepatobiliary disorders including cholangiocarcinoma in clinical practice.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present teachings will be apparent to those skilled in the art from consideration of the present specification and practice of the present teachings disclosed herein. It is intended that the present specification and examples be considered as exemplary only.

What is claimed is:

1. A method of detecting an abnormal amount of a biomarker associated with biliary tract cancer in a subject comprising: a) quantitating an amount of said biomarker associated with biliary tract cancer by quantitating an amount of a fragment of prothrombin having an m/z value of about 4204 m/z in a biological sample from the subject using mass spectrometry; and b) comparing the quantitated value obtained in (a) with a threshold value; wherein an abnormal amount of the biomarker is present in the biological sample when the quantitated value exceeds the threshold value.

2. The method of claim 1, wherein the biomarker is a fragment of prothrombin having the amino acid sequence of SEQ ID NO: 2.

3. The method of claim 2, further comprising c) identifying that the subject has biliary tract cancer when the quantitated value exceeds the threshold value.

4. The method of claim 1, wherein the mass spectrometry is matrix-associated laser desorption ionization time-of-flight mass spectrometry MALDI-TOF MS.

5. The method of claim 1, wherein the biological sample is blood serum.

6. The method of claim 2, wherein the threshold value is at least 322 AU.

7. A method of detecting biliary tract cancer in a subject comprising: a) quantitating an amount of a fragment of prothrombin in a sample from the subject using mass spectrometry, wherein the fragment of prothrombin has an m/z value of about 4204 m/z; and b) comparing the quantitated value obtained in (a) with a threshold value; wherein biliary tract cancer is detected when the quantitated value exceeds the threshold value.

8. The method of claim 7, wherein the mass spectrometry is matrix-associated laser desorption ionization time-of-flight mass spectrometry (MALDI-TOF MS).

9. The method of claim 7, further comprising quantitating at least one additional biomarker in the sample from the subject.

10. The method of claim 9, wherein the at least one additional biomarker is carbohydrate antigen 19-9 (CA 19-9).

11. The method of claim 9, wherein the at least one additional biomarker is carcinoembryonic antigen (CEA).

* * * * *

SEQUENCE LISTING

```
<160> NUMBER OF SEQ ID NOS: 2

<210> SEQ ID NO 1
<211> LENGTH: 622
<212> TYPE: PRT
<213> ORGANISM: Human

<400> SEQUENCE: 1

Met Ala His Val Arg Gly Leu Gln Leu Pro Gly Cys Leu Ala Leu Ala
1               5                   10                  15

Ala Leu Cys Ser Leu Val His Ser Gln His Val Phe Leu Ala Pro Gln
            20                  25                  30

Gln Ala Arg Ser Leu Leu Gln Arg Val Arg Arg Ala Asn Thr Phe Leu
        35                  40                  45

Glu Glu Val Arg Lys Gly Asn Leu Glu Arg Glu Cys Val Glu Glu Thr
    50                  55                  60

Cys Ser Tyr Glu Glu Ala Phe Glu Ala Leu Glu Ser Ser Thr Ala Thr
65                  70                  75                  80

Asp Val Phe Trp Ala Lys Tyr Thr Ala Cys Glu Thr Ala Arg Thr Pro
                85                  90                  95

Arg Asp Lys Leu Ala Ala Cys Leu Glu Gly Asn Cys Ala Glu Gly Leu
            100                 105                 110

Gly Thr Asn Tyr Arg Gly His Val Asn Ile Thr Arg Ser Gly Ile Glu
        115                 120                 125

Cys Gln Leu Trp Arg Ser Arg Tyr Pro His Lys Pro Glu Ile Asn Ser
    130                 135                 140
```

```
Thr Thr His Pro Gly Ala Asp Leu Gln Glu Asn Phe Cys Arg Asn Pro
145                 150                 155                 160

Asp Ser Ser Thr Thr Gly Pro Trp Cys Tyr Thr Thr Asp Pro Thr Val
            165                 170                 175

Arg Arg Gln Glu Cys Ser Ile Pro Val Cys Gly Gln Asp Gln Val Thr
            180                 185                 190

Val Ala Met Thr Pro Arg Ser Glu Gly Ser Ser Val Asn Leu Ser Pro
            195                 200                 205

Pro Leu Glu Gln Cys Val Pro Asp Arg Gly Gln Gln Tyr Gln Gly Arg
        210                 215                 220

Leu Ala Val Thr Thr His Gly Leu Pro Cys Leu Ala Trp Ala Ser Ala
225                 230                 235                 240

Gln Ala Lys Ala Leu Ser Lys His Gln Asp Phe Asn Ser Ala Val Gln
                245                 250                 255

Leu Val Glu Asn Phe Cys Arg Asn Pro Asp Gly Asp Glu Glu Gly Val
                260                 265                 270

Trp Cys Tyr Val Ala Gly Lys Pro Gly Asp Phe Gly Tyr Cys Asp Leu
        275                 280                 285

Asn Tyr Cys Glu Glu Ala Val Glu Glu Thr Gly Asp Gly Leu Asp
290                 295                 300

Glu Asp Ser Asp Arg Ala Ile Glu Gly Arg Thr Ala Thr Ser Glu Tyr
305                 310                 315                 320

Gln Thr Phe Phe Asn Pro Arg Thr Phe Gly Ser Gly Glu Ala Asp Cys
                325                 330                 335

Gly Leu Arg Pro Leu Phe Glu Lys Lys Ser Leu Glu Asp Lys Thr Glu
                340                 345                 350

Arg Glu Leu Leu Glu Ser Tyr Ile Asp Gly Arg Ile Val Glu Gly Ser
                355                 360                 365

Asp Ala Glu Ile Gly Met Ser Pro Trp Gln Val Met Leu Phe Arg Lys
370                 375                 380

Ser Pro Gln Glu Leu Leu Cys Gly Ala Ser Leu Ile Ser Asp Arg Trp
385                 390                 395                 400

Val Leu Thr Ala Ala His Cys Leu Leu Tyr Pro Pro Trp Asp Lys Asn
                405                 410                 415

Phe Thr Glu Asn Asp Leu Leu Val Arg Ile Gly Lys His Ser Arg Thr
                420                 425                 430

Arg Tyr Glu Arg Asn Ile Glu Lys Ile Ser Met Leu Glu Lys Ile Tyr
            435                 440                 445

Ile His Pro Arg Tyr Asn Trp Arg Glu Asn Leu Asp Arg Asp Ile Ala
            450                 455                 460

Leu Met Lys Leu Lys Lys Pro Val Ala Phe Ser Asp Tyr Ile His Pro
465                 470                 475                 480

Val Cys Leu Pro Asp Arg Glu Thr Ala Ala Ser Leu Leu Gln Ala Gly
                485                 490                 495

Tyr Lys Gly Arg Val Thr Gly Trp Gly Asn Leu Lys Glu Thr Trp Thr
            500                 505                 510

Ala Asn Val Gly Lys Gly Gln Pro Ser Val Leu Gln Val Val Asn Leu
            515                 520                 525

Pro Ile Val Glu Arg Pro Val Cys Lys Asp Ser Thr Arg Ile Arg Ile
            530                 535                 540

Thr Asp Asn Met Phe Cys Ala Gly Tyr Lys Pro Asp Glu Gly Lys Arg
545                 550                 555                 560

Gly Asp Ala Cys Glu Gly Asp Ser Gly Gly Pro Phe Val Met Lys Ser
```

```
                     565                 570                 575
Pro Phe Asn Asn Arg Trp Tyr Gln Met Gly Ile Val Ser Trp Gly Glu
            580                 585                 590

Gly Cys Asp Arg Asp Gly Lys Tyr Gly Phe Tyr Thr His Val Phe Arg
        595                 600                 605

Leu Lys Lys Trp Ile Gln Lys Val Ile Asp Gln Phe Gly Glu
    610                 615                 620

<210> SEQ ID NO 2
<211> LENGTH: 37
<212> TYPE: PRT
<213> ORGANISM: Human

<400> SEQUENCE: 2

Thr Phe Gly Ser Gly Glu Ala Asp Cys Gly Leu Arg Pro Leu Phe Glu
1               5                   10                  15

Lys Lys Ser Leu Glu Asp Lys Thr Glu Arg Glu Leu Leu Glu Ser Tyr
            20                  25                  30

Ile Asp Gly Arg Ile
            35
```